United States Patent
Siman-Tov et al.

(12) 
(10) Patent No.: US 6,276,155 B2
(45) Date of Patent: Aug. 21, 2001

(54) PERSONAL COOLING APPARATUS AND METHOD

(75) Inventors: Moshe Siman-Tov; Jerry Allen Crabtree, both of Knoxville, TN (US)

(73) Assignee: U T Battelle LLC, Oak Ridge, TN (US)

( * ) Notice: Subject to any disclaimer, the term of this patent is extended or adjusted under 35 U.S.C. 154(b) by 0 days.

(21) Appl. No.: 09/747,799

(22) Filed: Dec. 22, 2000

Related U.S. Application Data

(62) Division of application No. 09/397,685, filed on Sep. 16, 1999.

(51) Int. Cl.$^7$ ............................... F25D 23/12; F28F 7/00
(52) U.S. Cl. ............................................. 62/259.3; 165/46
(58) Field of Search .................................. 62/259.3, 420, 62/316; 165/46

(56) References Cited

U.S. PATENT DOCUMENTS

| | | |
|---|---|---|
| 3,982,134 | 9/1976 | Housholder et al. . |
| 4,572,864 | 2/1986 | Benson et al. . |
| 4,612,046 | 9/1986 | Orcutt . |
| 4,852,645 | 8/1989 | Coulon et al. . |
| 5,113,666 | 5/1992 | Parrish et al. . |
| 5,255,390 | 10/1993 | Gross et al. . |
| 5,269,369 | 12/1993 | Faghri . |
| 5,289,695 | 3/1994 | Parrish et al. . |
| 5,320,164 * | 6/1994 | Szczesuil et al. ........................ 165/46 |
| 5,323,843 | 6/1994 | Olszewski et al. . |
| 5,385,873 | 1/1995 | MacNeill . |
| 5,386,701 * | 2/1995 | Cao ....................................... 62/259.3 |
| 5,415,222 * | 5/1995 | Colvin et al. ............................ 165/46 |
| 5,564,124 * | 10/1996 | Elsherif et al. .................. 62/259.3 X |
| 5,626,665 | 5/1997 | Barger . |
| 5,722,482 | 3/1998 | Buckley . |
| 5,806,588 | 9/1998 | Weeks, Jr. et al. . |
| 5,818,693 | 10/1998 | Garner et al. . |
| 5,867,999 * | 2/1999 | Bratton et al. ....................... 62/259.3 |
| 5,898,570 | 4/1999 | Koon et al. . |

* cited by examiner

*Primary Examiner*—Henry Bennett
*Assistant Examiner*—Chen-Wen Jiang
(74) *Attorney, Agent, or Firm*—Oscar A. Towler, III; Hardaway/Mann IP Group

(57) ABSTRACT

A portable lightweight cooling apparatus for cooling a human body is disclosed, having a channeled sheet which absorbs sweat and/or evaporative liquid, a layer of highly conductive fibers adjacent the channeled sheet; and, an air-moving device for moving air through the channeled sheet, wherein the layer of fibers redistributes heat uniformly across the object being cooled, while the air moving within the channeled sheet evaporates sweat and/or other evaporative liquid, absorbs evaporated moisture and the uniformly distributed heat generated by the human body, and discharges them into the environment. Also disclosed is a method for removing heat generated by the human body, comprising the steps of providing a garment to be placed in thermal communication with the body; placing a layer of highly conductive fibers within the garment adjacent the body for uniformly distributing the heat generated by the body; attaching an air-moving device in communication with the garment for forcing air into the garment; removably positioning an exchangeable heat sink in communication with the air-moving device for cooling the air prior to the air entering the garment; and, equipping the garment with a channeled sheet in communication with the air-moving device so that air can be directed into the channeled sheet and adjacent the layer of fibers to expell heat and moisture from the body by the air being directed out of the channeled sheet and into the environment. The cooling system may be configured to operate in both sealed and unsealed garments.

26 Claims, 3 Drawing Sheets

PERSONAL COOLING APPARATUS AND METHOD

This appln is a Div of Ser. No. 09/397,685 filed Sep. 16, 1999.

The U.S. Government has rights in this invention pursuant to contract number DE-AC05-96OR22464 between Lockheed Martin Energy Research Corporation and the Department of Energy.

FIELD OF THE INVENTION

The present invention relates to a portable cooling device generally used with body armor systems and which is designed to utilize the body's natural cooling process of convection and the evaporation of sweat and/or other evaporative liquid to provide cooling and comfort to the person wearing the garment while being lightweight, thin, and flexible.

BACKGROUND OF THE INVENTION

Body armor systems, including vests worn by law enforcement officers, use Kevlar® or similar fibers, which are coated in plastic, as a projectile-resistant shield. The plastic coating is necessary to assure the safe performance of the vest, but makes the garment hot and uncomfortable to wear. This, in turn, decreases the mobility and, thus, the efficiency of the officers who wear them and acts as a deterrent to using the body armor and as a result, increases officer casualties. There have been several attempts to provide a more comfortable protective garment. For example, Parrish et al (U.S. Pat. No. 5,113,666), teach a cooling device that can be incorporated into a person's apparel to permit the transfer of water vapor from the wearer's skin. Parrish et al (U.S. Pat. No. 5,111,668), a continuation-in-part of U.S. Patent U.S. Pat. No. 5,113,666, teach a sealed garment containing a working fluid in an evaporation section of the garment, vaporization occurring by heat generated from the person wearing the garment. Parrish et al (U.S. Pat. No. 5,289,695), a divisional of U.S. Pat. No. 5,111,668, teach cooling devices such as vests, pads or patches used in garments, including space suits, sealed hazardous material suits, and/or vests. All of these embodiments comprise of a desiccant layer which is utilized in the storage of the water vapor resulting from the evaporation process. In the present invention, however, the water vapor resulting from the evaporation process is discharged to the environment thus alleviating the requirement of storage and decreasing the weight and size of the cooling apparatus.

Other examples may also be found in Scaringe et al (U.S. Pat. No. 4,856,294), Szczesuil et al (U.S. Pat. No. 5,320,164), Faghri (U.S. Pat. No. 5,269,369), Garner (U.S. Pat. No. 5,818,693), Koon et al (U.S. Pat. No. 5,898,570), Coulon et al (U.S. Pat. No. 4,852,645), Buckley (U.S. Pat. No. 5,722,482), and Benson (U.S. Pat. No. 4,572,864), which are hereby incorporated by reference.

These cooling systems, however, remain heavy and uncomfortable to the wearer. Therefore, there remains room in the art for a portable, lightweight, thin, and flexible garment which will provide more comfortable thermal conditions under the armor vest (or similar vest type garments) and would induce people to wear them as necessary, and thereby reduce the occurrence of preventable injuries and fatalities.

OBJECTS OF THE INVENTION

It is an object of the present invention to provide a portable, lightweight, thin, flexible, comfortable and adaptable cooling device generally used in conjunction with a body armor protective garment.

It is another object of the present invention to provide a cooling device that uses the body's natural capabilities to cool itself by conduction, convection, and/or evaporation as a part of the garment's cooling system.

It is a further object of the present invention to provide a cooling garment that will make body armor protective garments more likely to be worn by those requiring such protection.

It is an even further object of the present invention to provide a cooling system operable in both sealed and unsealed garments.

These and other objects are achieved by a portable lightweight cooling apparatus for cooling an object, comprising some combination of a channeled sheet which absorbs sweat and/or other evaporative liquid, means for moving air through said channeled sheet, and a layer of highly conductive fibers adjacent to said channeled sheet wherein the layer of fibers uniformly distributes heat across the object being cooled, while the air moving within the channeled sheet evaporates sweat and/or other evaporative liquid, absorbs and discharges the heat and moisture generated by the object into the environment.

These and other objects are also achieved by a method for removing heat generated by the human body, comprising the steps of providing a garment to be placed in thermal communication with the body; potentially placing a layer of conductive fibers within the garment adjacent the body for uniformly distributing the heat generated by the body; removably attaching means for moving air in communication with the garment for forcing air into the garment; potentially including an exchangeable heat sink in communication with the means for moving air in order to precondition the air prior to the air entering the garment or becoming in communication with the layer of highly conductive fibers to transfer heat from the body to the heat sink; and, potentially equipping the garment with a channeled sheet in communication with the air-moving device such that air is directed into the channeled sheet adjacent the layer of fibers so that heat and moisture are expelled from the body by the air being directed out of the channeled sheet and into the environment.

SUMMARY OF THE INVENTION

In accordance with one aspect of the present invention, the foregoing and other objects are achieved by an apparatus for cooling a living body which apparatus comprises: a layer of thermally conductive material; and a heat sink operably connected to said thermally conductive layer, the apparatus being configured to cause heat from the living body to be conducted through the thermally conductive layer and to the heat sink when the living body is proximate the thermally conductive layer.

In accordance with a second aspect of the present invention, the foregoing and other objects are achieved by an apparatus for cooling a living body which comprises: a channeled sheet capable of absorbing evaporative liquid; and means for moving air into and through said channeled sheet and communicably connected thereto; said apparatus configured so that when the living body is proximate the channeled sheet the channeled sheet may absorb evaporative liquid from the living body and air moving through said channeled sheet may vaporize the evaporative liquid.

In accordance with a third aspect of the present invention, the foregoing and other objects are achieved by a method for removing heat generated by a body, comprising the steps of: providing an apparatus including a garment, a layer of thermally conductive material disposed within said garment, and a heat sink connected to said thermally conductive material to permit conduction of heat therebetween; and placing the thermally conductive material in contact with at least a portion of the body to cause the thermally conductive material to conduct heat from the body to the heat sink.

In accordance with a fourth aspect of the present invention, the foregoing and other objects are achieved by a method for removing heat generated by a body, comprising the steps of: providing an apparatus comprising a garment, a channeled sheet for absorbing evaporative liquid disposed within said garment, and a powered air moving device disposed for moving air through channels within said channeled sheet; placing the channeled sheet in contact with at least a portion of the body; and causing the air-moving device to direct air through the channeled sheet and expel air therefrom whereby liquid from the body may be absorbed by the channeled sheet and evaporated to cool the body and whereby heat from the body may be convectively removed by the moving air.

In accordance with a fifth aspect of the present invention, the foregoing and other objects are achieved by an apparatus for cooling a living body which comprises: a continuous layer of thermally conductive material wherein a first portion of the continuous layer is configured to be proximate to the living body for absorbing heat from the body and a second portion of said layer is configured to be exposed to ambient air for discharging heat to the ambient air.

In accordance with a sixth aspect of the present invention, the foregoing and other objects are achieved by a body armor protective garment for protecting and cooling a living body which comprises a projectile-resisting shield and a continuous layer of thermally conductive material wherein a first portion of the layer is configured to be inside the shield proximate to the living body for absorbing heat from the body, and a second portion of said layer is configured to be outside said shield and exposed to ambient air for discharging heat to the ambient air.

DETAILED DESCRIPTION OF THE INVENTION

The present invention is a cooling system integrated into a garment that uses the body's natural capability to cool itself through convection and sweat evaporation. In a preferred embodiment illustrated in FIGS. 1–4a and 5, the garment cooling system comprises a sheet of hydrophillic material having a plurality of channels formed therein, an air moving device that introduces outside air into the plurality of channels, and a layer that interfaces between the human skin and the channeled sheet to absorb perspiration. In an alternative embodiment illustrated in FIGS. 4b and 5, the garment cooling system comprises a thermal energy storage TES) capsule that is coupled to carbon fiber fabric. Although the cooling system will be described in terms of its use as part of a bullet proof vest, it is apparent that the cooling system could be used in fire-proof protective suits, chemical and biological suits, diving suits, hospital blankets, tents and other personal equipment where a means for cooling might be employed.

Figure 1:
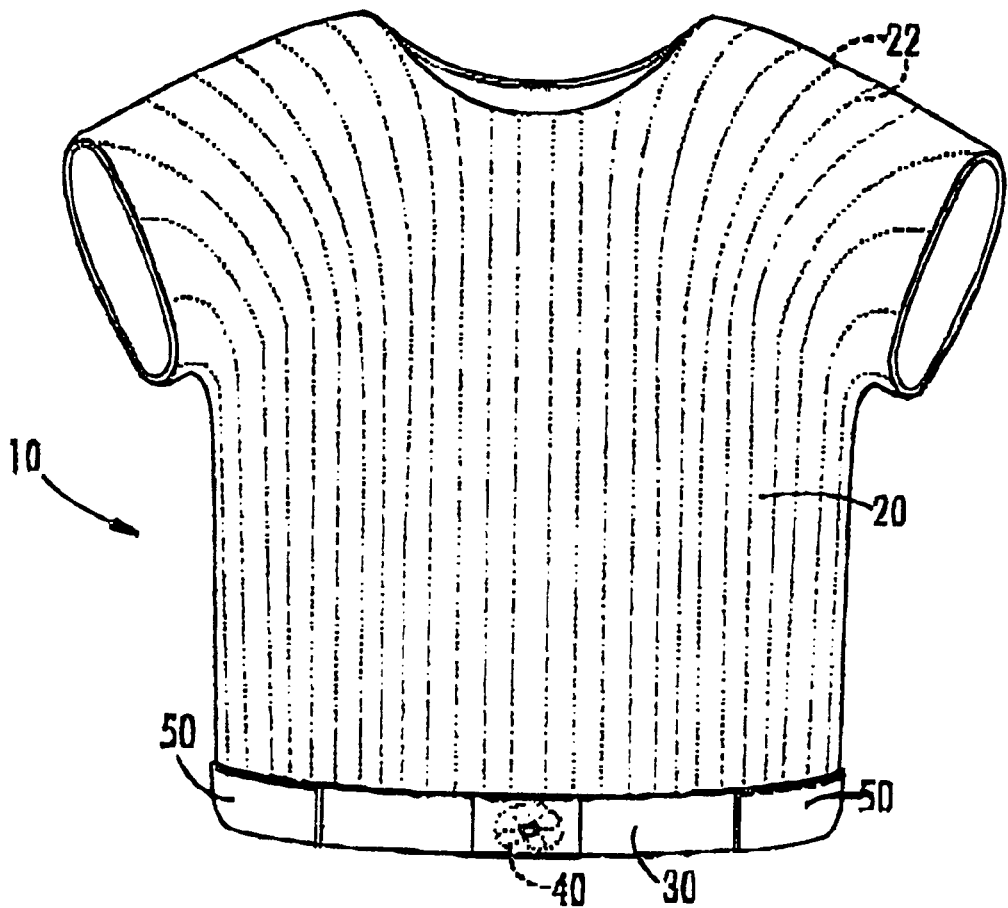
FIG. 1 is a perspective view of the garment, according to a preferred embodiment of the present invention.

Referring to FIG. 1, a garment, generally referred to by reference number 10, having a cooling system according to a preferred embodiment of the present invention is formed in the shape of a vest 20 connected to a belt 30. Although it is appreciated that a vest may be appropriate for certain applications, cooling system could easily be adapted for use in pants, shirts, skirts, hats and other like garments. In the vest configuration illustrated in FIG. 1, belt 30 has a plurality of openings 32 (FIG. 3) formed therein that are placed in fluid communication with a plurality of channels 22 formed within vest 20. An air moving device 40, such as a mini-fan, blower, impeller or like device, is carried by belt 30 so that air is circulated within plurality of channels 22. Belt 30 and openings 32 therefore serve as a manifold for distributing air to channels. Each opening of plurality of openings 32 places air from air moving means 40 in fluid communication with plurality of channels 22 within vest 20 to distribute the flow of air created by air moving device 40 throughout gament 10. Importantly, air moving device 40 brings air from the outside environment into gament 10. Air flows close to the skin absorbing both heat and moisture and, thereby, cooling the human body in a way that takes advantage of the natural process of perspiring. The metabolic heat generated by the body is carried out of channels 22 and is exhausted to the outside environment.

Optionally, a cooling means 50, which is essentially a heat sink, as will be described in more detail below, is positioned between air moving device 40 and channels 22 to condition the outside air prior to its entering channels 22. Cooling means 50 is used only for partial cooling of outside air in climates where outside air temperature is unacceptably high. Depending upon the particular climate in which garment is being used, cooling means 50 may not be required. In the event use of cooling means is not desired, garment 10 may be designed such that carbon fiber wraps around to the outside of vest and the environment serves as the heat sink. In climates where humidity is high, cooling means 50 may serve as a dehumidifier, extracting moisture from the air during the cooling process via condensation on the cool walls of cooling means 50 or via an absorbing material. Cooling means 50 is used only for partial cooling of outside air in climates where outside air temperature is unacceptably high. Depending upon the particular climate in which garment is being used, cooling means 50 may not be required. In the event use of cooling means is not desired, garment 10 may be designed such that carbon fiber wraps around to the outside of vest and the environment serves as the heat sink. In climates where humidity is high, cooling means 50 may serve as a dehumidifier, extracting moisture from the air during the cooling process via condensation on the cool walls of cooling means 50 or via an absorbing material.

Figure 2:
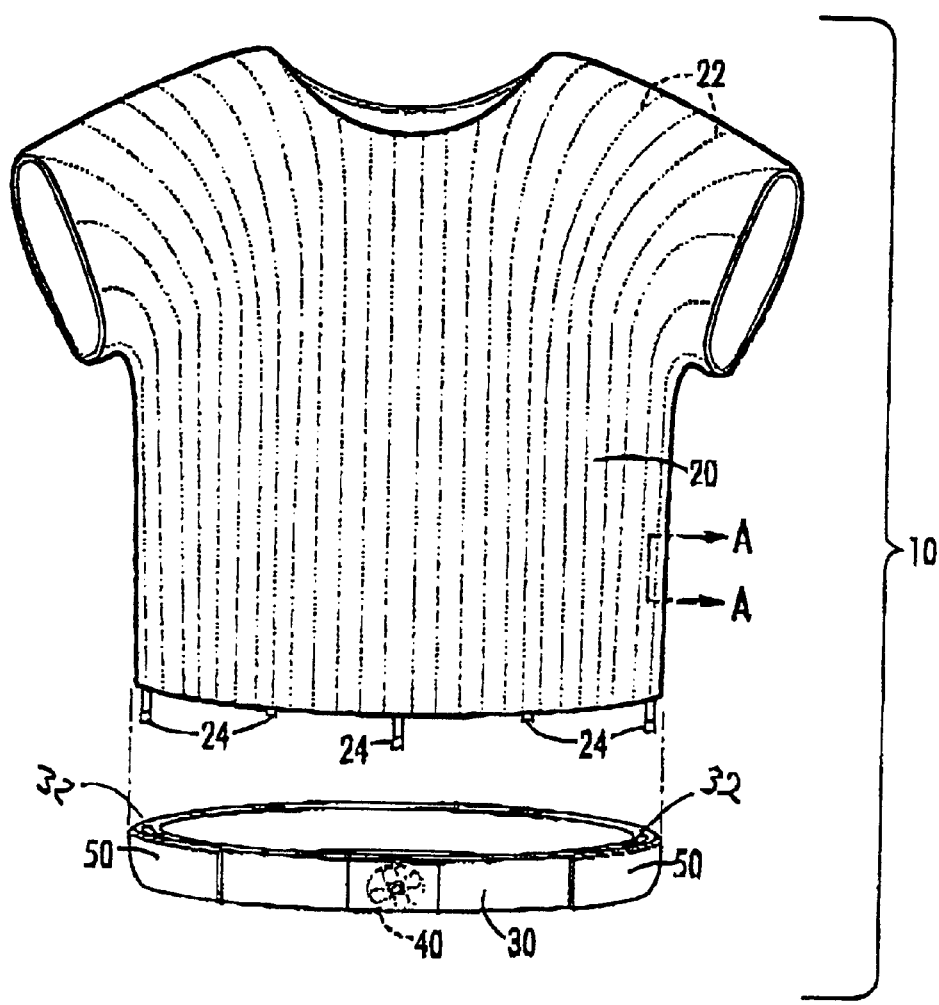
FIG. 2 is an exploded, perspective view of the garment, according to a preferred embodiment of the present invention.
Figure 3:
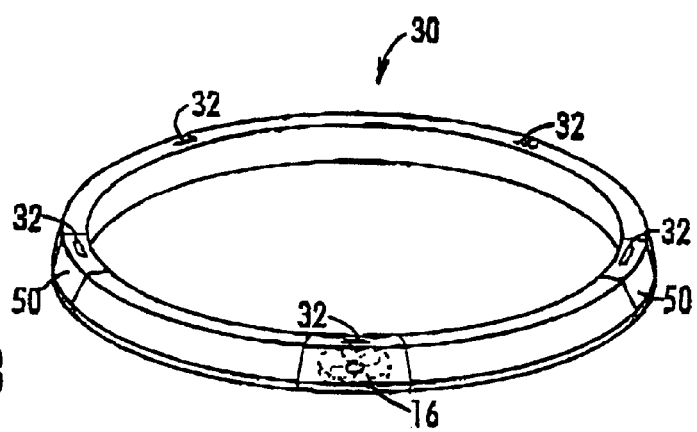
FIG. 3 is a top perspective view of the cooling belt, according to a preferred embodiment of the present invention.
Figure 4A:
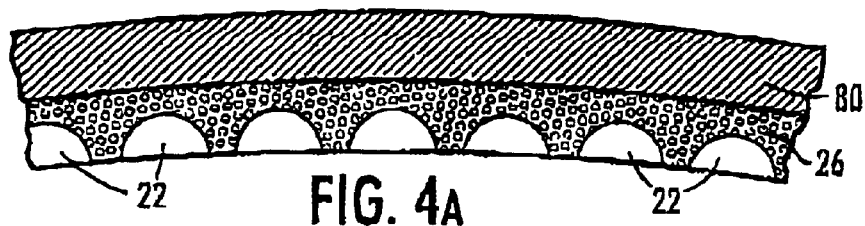
FIG. 4a is a cross-sectional view of the garment along line A—A as shown in FIG. 2, according to a preferred embodiment of the present invention.
Figure 4B:
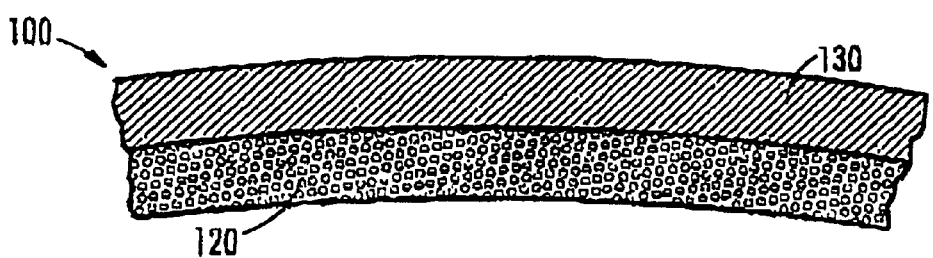
FIG. 4b is a detailed cross-sectional view of the garment, according to a preferred embodiment of the present invention.

Referring to FIGS. 2 and 3, belt 30 is capable of detachment from vest 20 by releasing fastening means 24. Fastening means 24 may comprise a male-type connection or fitting, or other suitable fastening means such as snaps, adhesives and the like, and is hollow to receive air from openings 32 and deliver air to channels 22. Cooling means 50, which is preferably TES material, is placed in belt 30 at openings 32 so that it can remove some heat from incoming air before it enters fastening means 24 and channels 22. Cooling means 50 serves to lower the temperature of incoming air by a few degrees to take up only part of the heat load. It will be appreciated by those of ordinary skill in the art that air moving means 40 and cooling means 50 could be incorporated into vest 20, rather than using a separate belt 30. Referring to FIG. 4A, vest 20 is formed from a sheet 26 having a plurality of channels 22, each of which allows the flow of air through garment 10. A protective layer 80, such as a layer of KEVLAR manmade fibers is worn over sheet 26. Channels 22 are preferably formed in a manner that minimizes pressure drop. Sheet 26 is preferably formed from a lightweight and flexible hydrophilic materials, such as porous plastics or felted foams, so that sweat, and other evaporative liquids are wicked throughout sheet 26. Sheet 26 may be worn in contact with the skin of the wearer, or, alternatively, may be worn over an undergarment, and the undergarment may be intentionally wetted prior to use or may become wetted by sweat from the user. As herein used, wearing garment 10 "proximate to the body" of its user includes wearing garment in direct contact with the skin or in contact with any garment between the skin and sheet 26. Sheet 26 may be incorporated into a CoolMax® type garment for structural support of channels.

Optionally, sheet 26 may be further enhanced by introducing carbon fiber "needles," or other highly conductive material, into sheet 26 during the molding process. The resulting 26 sheet would then be better adapted to wick the sweat, and/or other evaporative liquid, all through channels 22 as well as having a much-improved thermal conductivity so as to be able to redistribute the heat more uniformly throughout vest 20. The combination of carbon fibers and moving air is another important feature of the present invention because the combination is so effective in removing heat from hot areas very efficiently. To prolong the useful life, sheet 26 can also be enhanced by the addition of anti-microbial agents, such as those sold under the trademark MICROBAN, incorporated into the material from which it is made. Further, sheet 26 can be enhanced with the addition of phase change material that could preclude the use of cooling means 50 in belt 30.

An alternative embodiment of a garment 100 comprising a carbon fiber fabric 120 coupled to a TES material, and then covered with a protective layer 130 such as a layer of KEVLAR manmade fibers. This alternative embodiment may be used for applications in which duty cycles are less demanding and where weight is not as much of a factor. In this instance, cooling will depend on conduction and the TES capsule and not on air flow. To ensure adequate operation of garment 100, a transition coupling (not shown) between TES capsules and carbon fiber fabric is necessarily provided. This coupling connects the flexible carbon fiber impregnated fabric 120 to the rigid TES capsule and, thus, requires a flexible to semi-rigid to rigid transition. Although this may be achieved in many possible ways, it is also imperative that the thermal conductivity of this coupling or transition does not impair or impede the conductivity of garment 100. Coupling could be an adhesive, having a high thermal conductivity, that secures TES capsules to carbon fiber fabric 120.

Figure 5:
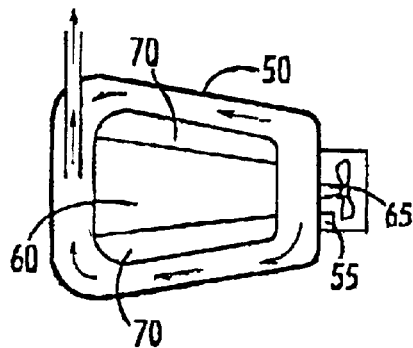
FIG. 5 is a perspective view of the thermal energy storage (TES) capsule in the cooling belt, according to a preferred embodiment of the present invention.

Preferably, air is conditioned prior to being introduced into plurality of channels 22 using a TES capsule 60, which is best illustrated in FIG. 5. TES capsule 60 is preferably formed from aluminum or other highly conductive, lightweight material and is preferably located within belt 30. TES capsule will 60 preferably contain a low melting temperature phase change material, for example, ice/water at zero degrees Celsius. The phase change material, however, may be any known TES type material which will meet the desired needs of the invention and the conditions of use. TES capsule 60 may also have cooling fins 70 made of aluminum, aluminum alloy, or some other highly conductive material for effective heat transfer and light weight. TES capsule 60 will serve primarily as a heat sink to cool the incoming outside air from its ambient temperature to a cooler but comfortable temperature prior to entering channels 22.

The airflow from air moving device 65 may adjusted manually or adjusted using an automatic integrated control system 55 (FIG. 5). Control system 55 is in operational connection with a thermostat (not shown), which controls the air flow of air moving device depending upon the desired temperature. Control system 55 is completely analogous to a home thermostat control, which turns on fans in response to an increase in temperature, but may have additional capabilities as well. For example, in conjunction with the adjustably controlled flow rate, the exposed surface of a TES 60 capsule 60 can be altered to maintain the exit temperature from TES capsule 60. Air-moving device 65 may be operated by lightweight rechargeable batteries, for example, lithium-ion batteries, nickel-cadmium batteries, nickel-metal-hydride batteries, and the like or conventional non-rechargeable batteries. Air moving device 65 operates in conjunction with TES 60 because it reduces the amount of TES material needed for cooling and results in a lighter weight garment 10. Prior art systems dump all the heat into a heat sink, and must therefore be sized for the maximum heat load, resulting in a much larger quantity of TES material than the present invention requires. Here, TES capsule 60 is only used for part of the load, the remained being taken care of by air moving device 65.

The present invention, thus, provides a lightweight, thin, flexible, and comfortable cooling garment which is adaptable to the circumstances of the user, and uses the body's natural capabilities to cool itself as a part of the garment's cooling system. The invention provides a cooling device for a protective garment which is operable in both sealed and unsealed garments.

In use, garment may be worn by a user to provide additional cooling. By manually operating air moving means 40 or using controller system to operate air moving means 40, air will be circulated through channels 22 close to the skin absorbing both heat and moisture, thereby cooling the human body. The metabolic heat generated is carried out of channels 22 and is exhausted to the environment.

It will be readily understood by those persons skilled in the art that the present invention is susceptible of broad utility and application. Many embodiments and adaptations of the present invention other than those described, as well as many variations, modifications and equivalent arrangements will be apparent from or reasonably suggested by the present invention and foregoing description thereof, without departing from the substance or scope of the present invention as defined by the following appended claims.

We claim:

1. An apparatus for cooling a living body, comprising:
    a channeled sheet capable of absorbing evaporative liquid; and, a means for moving air into and through said channeled sheet and communicably connected thereto, wherein said apparatus is configured so that when the living body is proximate the channeled sheet the channeled sheet may absorb evaporative liquid from the living body and air moving through said channeled sheet will aid in removing the evaporated liquid.

2. The apparatus of claim 1, wherein said channeled sheet comprises a plurality of tubular channels.

3. The apparatus of claim 1, wherein said channeled sheet comprises at least one material selected from the group consisting of polyethylene, polypropylene, ethylene vinyl acetate, and polyurethane.

4. The apparatus of claim 1, wherein said channeled sheet is impregnated with at least one material selected from the group consisting of carbon fiber needles and phase change materials.

5. The apparatus of claim 1, wherein said channeled sheet has at least one property selected from the group consisting of hydrophilic and anti-microbial.

6. The apparatus of claim 1, wherein said means for moving air is selected from the group comprising a fan, blower, impeller, and natural convection.

7. The apparatus of claim 1, wherein said means for moving air is manually controlled.

8. The apparatus of claim 1, wherein said means for moving air comprises a controller having at least one sensor selected from the group consisting of temperature sensor, relative humidity sensor, and wet-bulb temperature sensor.

9. The apparatus of claim 1, further comprising a garment for supporting said channeled sheet proximate the living body.

10. The apparatus of claim 9, further comprising an air conduit disposed between said garment and said means for moving air.

11. The apparatus of claim 10, wherein said air conduit comprises at least one tube.

12. The apparatus of claim 1 further comprising an electric power supply, said means for moving air connected to and driven by said electric power supply.

13. The apparatus of claim 12, wherein said electrical power supply further comprises at least one battery selected from the group consisting of lithium-ion battery, nickel-cadmium battery, nickel-metal-hydride battery, sealed lead acid battery, and alkaline battery.

14. The apparatus of claim 1, further comprising a heat sink disposed in communication with said means for moving air for preconditioning the air propelled by said means for moving air.

15. The apparatus of claim 14, wherein said heat sink comprises a thermal energy storage device.

16. The apparatus of claim 14, wherein said thermal energy storage device comprises an energy storage medium contained within an enclosure.

17. The apparatus of claim 16, wherein said enclosure comprises a material selected from the group consisting of aluminum and aluminum alloys.

18. The apparatus of claim 17, wherein said enclosure is thermally conductive and further comprises fins.

19. The apparatus of claim 16, wherein said thermal energy storage medium comprises water and said enclosure is configured to contain water in liquid phase, solid phase, and a combination thereof.

20. The apparatus of claim 14, wherein said heat sink is removably connected.

21. The apparatus of claim 1, further comprising a means for dehumidifying the air moved through said channeled sheet communicably connected to said means for moving air.

22. The apparatus of claim 1, further comprising a layer of thermally conductive material configured to be disposed between said channeled sheet and the living body to conduct heat across the living body.

23. The apparatus of claim 22, wherein said layer of thermally conductive material comprises carbon fibers.

24. A method for removing heat generated by a body, comprising the steps of:

providing an apparatus comprising a garment, a channeled sheet for absorbing evaporative liquid disposed within said garment, and a means for moving air through channels within said channeled sheet;

placing the channeled sheet in contact with at least a portion of the body; and causing the air-moving device to direct air through the channeled sheet and expel air therefrom whereby liquid from the body may be absorbed by the channeled sheet and evaporated to evaporatively cool the body and heat from the body is convectively removed by the moving air.

25. The method of claim 24 wherein the apparatus further comprises a heat sink disposed in communication with said air moving device for preconditioning the air moving therethrough.

26. The method of claim 24 wherein the apparatus further comprises a layer of conductive material which distributes heat across the body and channel sheet disposed in surface contact between said channeled sheet and at least a portion of the body.

* * * * *